US00PP15077P2

(12) United States Plant Patent
Lee

(10) Patent No.: US PP15,077 P2
(45) Date of Patent: Aug. 10, 2004

(54) GENUS SPECIES RHODODENDRON HYBRID VARIETAL DENOMINATION 'ROBLEE'

(50) Latin Name: *Rhododendron hybrid*
Varietal Denomination: Roblee

(75) Inventor: Robert Edward Lee, Independence, LA (US)

(73) Assignee: Plant Development Services Inc., Loxley, AL (US)

( * ) Notice: Subject to any disclaimer, the term of this patent is extended or adjusted under 35 U.S.C. 154(b) by 15 days.

(21) Appl. No.: 10/679,205
(22) Filed: Oct. 6, 2003
(51) Int. Cl.[7] ..... A01H 5/00
(52) U.S. Cl. ..... Plt./240
(58) Field of Search ..... Plt./240, 239

*Primary Examiner*—Kent Bell

(57) ABSTRACT

A new and distinct variety of Azalea plant found as a branch sport of the Azalea hybrid 'Conlec' U.S. Plant Pat. No. 10,580. The new variety possesses a unique blooming time and is superior in development of an upright, dense, globose shaped plant with attractive large single pink flowers.

1 Drawing Sheet

Genus species: Rhododendron hybrid.
Varietal denomination: 'Roblee'.

BACKGROUND OF THE INVENTION

The present invention relates to a new and distinct variety of evergreen azalea of the genus Rhododendron and a member of the Ericaceae family. This new azalea variety, hereinafter referred to as 'Roblee', was discovered by Robert Edward Lee of Transcend Nursery in July, 1999 in Independence, La. 'Roblee' originated as a naturally occurring branch sport of Azalea hybrid 'Conlec' U.S. Plant Pat. No. 10,580 while it was being grown in Independence, La. The value of this new cultivar lies in its unique blooming period, bloom color, bloom form, bloom size, and growth habit.

Asexual propagation of the new plant by cuttings has been under Mr. Lee's direction at the same location. The new plant retains its distinctive characteristics and reproduces true to the type in successive generations. The plant cannot be reproduced true from seed.

SUMMARY OF THE INVENTION

The following are the most outstanding and distinguishing characteristics of this new cultivar when grown under normal horticultural practices in Independence, La.

1. The unique spring, summer, and fall blooming.
2. A pink flower color Red-Purple Group 67C with dotting color Red-Purple Group 64B.
3. Large, single flower with wavy petal margins. The flowers range in size from 3½"–4" in diameter.
4. Easily propagated with semi-hardwood cuttings in late spring through the summer.
5. Fast growth rate under normal fertilization and moisture conditions.
6. Upright, dense and globose in nature.
7. Good specimen plant.
8. Desirable in planters.
9. Makes a very good hedge or screen.
10. Very good foundation plant for large buildings.

11. Does well as an understory plant in a woodland garden.
12. Hardy to Zone 7.
13. Attracts butterflies.

DESCRIPTION OF THE DRAWINGS

This new Azalea hybrid variety is illustrated by the accompanying photographic prints in which:

1. The photograph at the top of the sheet is a close-up showing flower, foliage, and stem color as well as flower size and form.

2. The photograph at the bottom of the sheet shows the dense, upright and globose growth habit of a young three gallon plant.

The colors shown are as true as is reasonably possible to obtain by conventional photographic procedures. Colors in the photographs may appear different than actual colors due to light reflectance. The colors of the various plant parts are defined with reference to The Royal Horticultural Society Colour Chart. Description of colors in ordinary terms are presented where appropriate for clarity in meaning.

BOTANICAL DESCRIPTION OF THE PLANT

The following is a detailed description of the new variety of Azalea based on my observations made of 2 year old plants grown in 3 gallon containers in wholesale commercial production practices, in greenhouses, and in established landscape plantings in Independence, La.

Distinctive characteristics:

TABLE 1

| Characteristic | 'Roblee' | 'Conlec' PP#10580 | R.oldhamil 'Fourth of July' | 'Georgia Giant' |
|---|---|---|---|---|
| Height (Mature) | 5–6' | 5–6' | 8–10' | 5–6' |
| Width (Mature) | 5–6' | 5–6' | 6–7' | 4–5' |
| Flower Diameter | 3½–4" | 3½–4" | 1¾–3¼" | 4–5½" |
| Flower Form | Single | Single | Single | Single |
| Flower Color | Red-Purple G. 67C | Red-Purple G. 71C | Red G. 39A | White G. 155D |

TABLE 1-continued

| Characteristic | 'Roblee' | 'Conlec' PP#10580 | R.oldhamil 'Fourth of July' | 'Georgia Giant' |
|---|---|---|---|---|
| Flowers per Terminal | 2–3 | 2–3 | 2–4 | 1–4 |
| Bloom Period | April | April | Early July> Frost | May |
| " | Late July> Frost | Late July> Frost | | |
| Hardy Zone | 7 | 7 | 7 | 7 |
| Stamen Number | 8–10 | 8–10 | 7–10 | 8–10 |

'Roblee' originated as a branch sport of Azalea hybrid 'Conlec' U.S. Plant Pat. No. 10,580 which was the result of Mr. Lee's planned cross hybridization between the Azalea 'Georgia Giant' (unpatented) and *Rhododendron oldhamii* 'Fourth of July' (unpatented). The new variety differs from 'Conlec' in its flower color which is Red-Purple Group 67C rather than Red-Purple Group 71C.

Mr. Lee's hybridization program was conducted with emphasis on species that are not commonly found in the genetic make-up of the present day hybrids. The 'Fourth of July' cultivar is a heavy summer and fall blooming plant, not like the Rhododendron Species Foundation form. The flower buds form on new growth and start blooming about July 14. Mr. Lee used this cultivar to cross with existing hybrids which have a tendency to bloom in the fall and which are also fairly hardy. As expected the resulting seedlings are heavy summer and fall bloomers with very impressive spring blooms also.

Classification:

Botanical: Rhododendron hybrid 'Roblee'.

Form: Upright, dense, and rounded.

Height: 5–6'.

Width: 5–6'.

Growth habit: Upright, dense and globose. Fast growth rate under normal fertilization and moisture conditions.

Growth rate: In a period of six years from a rooted cutting the plant reaches a height of 4 feet and a spread of 3 feet. The growth rate is normally about 10 to 12" per year, the plant reaches a height of 5 to 6' at maturity while maintaining a dense habit due to the abundant branch development.

Foliage: Alternate, simple, evergreen, pubescent, elliptic, and varying in size from 2¼" to 2¾" long and ¾" to 1⅛" wide. The margins are entire, with a petiole ⅜" to ½" long. Midveins and laterals are impressed on the upper leaf surface and prominent on the underside. The base of the leaf is cuneate to attenuate and the apex is acute to mucronate. The upper surface of the immature leaves is dull, pubescent, and is Yellow-Green Group 144A and the underside is Yellow-Green Group 146D, pubescent, and matte. The upper surface of the mature leaves is Yellow-Green Group 147A, dull and slightly pubescent and the underside is Yellow-Green Group 146B, matte, and pubescent. The immature petioles, midribs, and veins are Yellow-Green Group 146C. New growth is pubescent. These hairs are initially soft and white and cover both sides of the leaf with a higher concentration on the petioles and veins. They are slightly curled, flat, and range in length from 1/32" to ⅛". As the growth matures much of the leaf pubescence is lost; however, the stems, petioles, and leaf veins retain this pubescence which becomes more setaceous and darker in color (Brown Group 200A) through the growing season.

In 2001, the date of initial spring growth was March 8, in Independence, La. After the initial spring flush there was almost continuous growth until that fall ending November 5, also in Independence, La. When grown in full sun, the internode length of this plant is ⅝" to 1"; when grown in light shade the internode length is ⅞" to 1¼". As would be expected a plant grown in shade results in a taller, less dense plant with larger leaves.

The average length of terminal growth of the initial spring flush is about 6" for a plant in full sun and about 8" when grown in shade. This growth should not be trimmed since it will produce flowers starting in late July. As the plant continues to grow through the summer and fall more flower buds are produced, which mature and bloom until frost. This remaining growth produces about 5" to 6" of height. As cool weather approaches, some of the flower buds become dormant. These buds bloom in April of the next year.

Stems: The young stems are Yellow-Green Group 146C and densely clothed with spreading white glandular hairs intermixed with scattered spreading, flattened hairs. During the second growing season they become Greyed-Green Group 197B, glabrous and rugose. The pith is solid and uniform. Young and older stems are densely branched.

Buds: Tight buds at ½" are ovate and acuminate Yellow-Green Group 146D with a hairy pubescence Brown Group 200A. The buds are borne in clusters of 2 to 3, and are sheathed by a pair of modified leaf bracts which are from ¼" to ⅝" long, persistent, and Yellow-Green Group 147A. The pedicel is ½" to ⅝" long, heavily pubescent, and Red Group 47B. The calyx is ⅜" to ½" long, Yellow-Green Group 144A, funnel shaped, persistent, and pubescent. The five imbricated sepals are lanceolate and joined at the base to form a cup. As the buds swell the bud sheath matures to a Greyed-Orange Group 165A, falls off, and reveals the flower color Red-Purple Group 67A.

Flowers: Perfect, single, Red-Purple Group 67C upper surface, Red-Purple Group 64D under surface, glabrous, open funnel shaped, 3½" to 4" in diameter by 2½" to 2¾" in depth, borne on current season's growth, non-fragrant; they last on the plant in the garden 5 to 6 days. There are five petals which are fused at the base, elliptic to obovate, and have wavy margins. These petals are 2¾" to 3¼" long, 1¼" to 1¾" wide, and have rounded apexes and entire margins. Three out of five petals are dotted with Red-Purple Group 64B. There are 8 to 10 stamens which are 1½" to 2" long. The filaments are Red-Purple Group 68B, the anthers are Red-Purple Group 59A, and the pollen matures to Yellow Group 11B. The pistil is single, non-petaloid, 1¾" to 2¼" long and Red Group 54A. The ovary is densely glandular-setose and has five locules. The capsule matures in about 5 months, in Independence, La., to about ¼" to ½" long; it has a persistant style, is Yellow-Green Group 147A, and contains from 100 to 400 nonwinged seeds. Normally fruit set is not heavy. There is a 2 to 3 week flowering period in April in Independence, La. Flowering resumes in late July as the new buds mature and continues until frost which can be as late as November or December in Independence, La. Azaleas blooming at this time of year attract butterflies in profusion.

Culture: Grows well in a wide range of conditions, tolerates sun to shade. Prefers a moist, well-drained soil that is rich in organic matter. Responds well to mulching and medium applications of fertilizer; prefers ph 5.0 to 5.5. Very little pruning is needed; adaptable to container and above ground planters; makes a good foundation plant or informal hedge with excellent foliage and flower contrast. Ideal for coastal regions and warmer parts of Piedmont. Propagated with semi-hardwood cuttings in late spring through the summer.

Pests: Lace wing and spider mites can be a problem.

I claim:

1. A new and distinct variety of Azalea plant named 'Roblee', as illustrated and described.

* * * * *

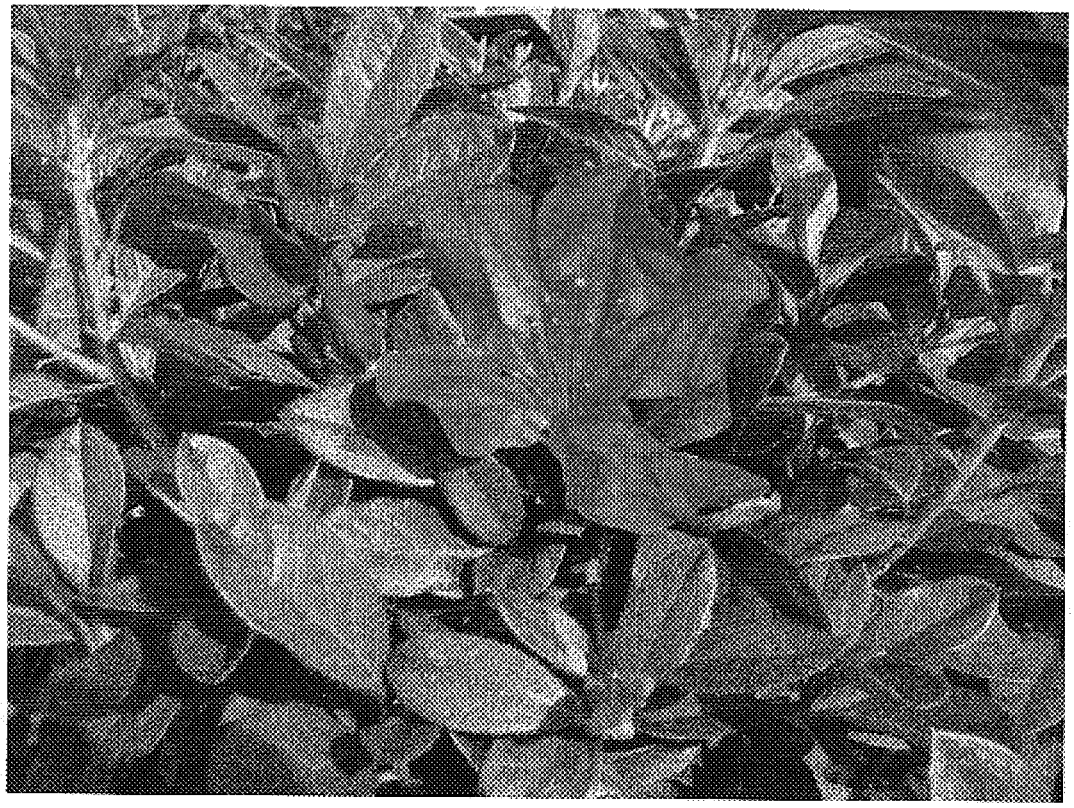
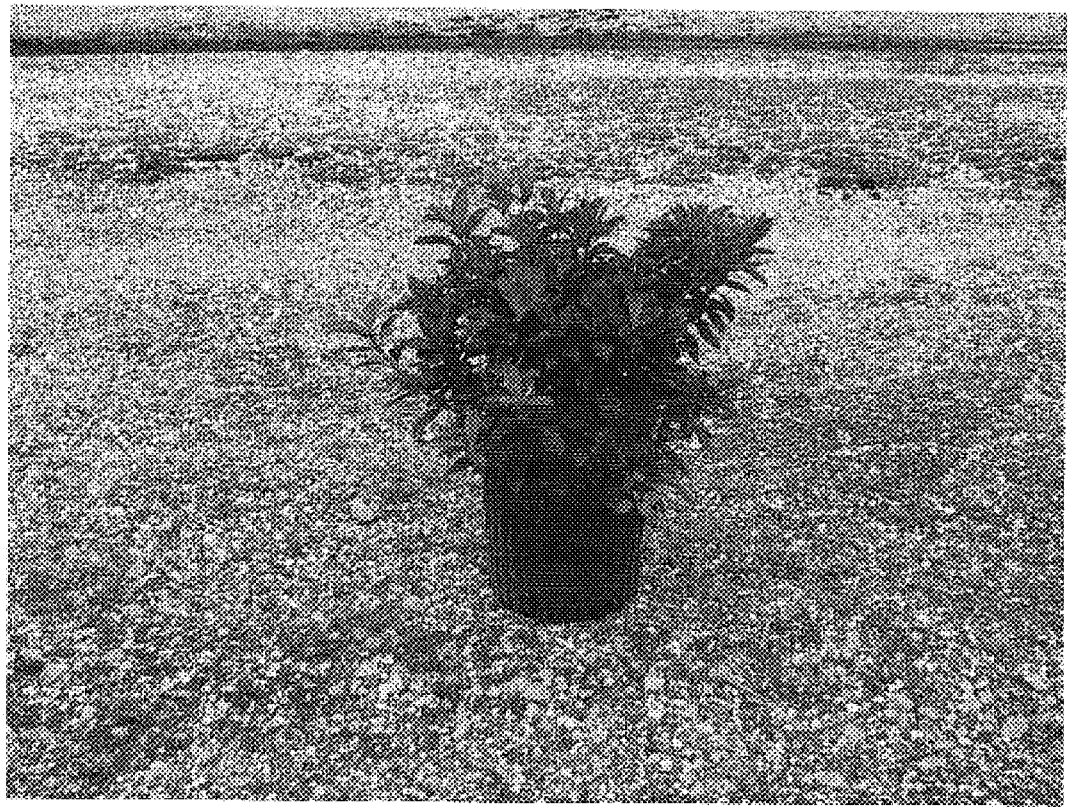

UNITED STATES PATENT AND TRADEMARK OFFICE
Certificate

Patent No. PP15,077 P2 Patented: August 10, 2004

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Flint Jerome Johnson, Mobile, AL (US).

Signed and Sealed this Thirtieth Day of June 2009.

ANNE M. GRUNBERG
*Supervisory Patent Examiner*
Art Unit 1661